US00PP29073P3

(12) United States Plant Patent
Koot

(10) Patent No.: US PP29,073 P3
(45) Date of Patent: Mar. 6, 2018

(54) ***CALIBRACHOA* PLANT NAMED 'DUEALCOHOPI'**

(50) Latin Name: ***Calibrachoa* sp.**
Varietal Denomination: Duealcohopi

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 53 days.

(21) Appl. No.: 14/999,795

(22) Filed: Jun. 28, 2016

(65) Prior Publication Data

US 2017/0374788 P1 Dec. 28, 2017

(51) Int. Cl.
*A01H 5/02* (2006.01)

(52) U.S. Cl.
USPC ..... Plt./413
CPC ..... *A01H 5/02* (2013.01)

(58) Field of Classification Search
USPC ..... Plt./413
See application file for complete search history.

*Primary Examiner* — Keith O Robinson
(74) *Attorney, Agent, or Firm* — C. A. Whealy

(57) ABSTRACT

A new and distinct cultivar of *Calibrachoa* plant named 'Duealcohopi', characterized by its compact, semi-upright to outwardly spreading, trailing and decumbent plant habit; freely branching habit; early and freely flowering habit; red purple-colored petals with a dark purple-colored central band and yellow-colored stripes; and good garden performance.

2 Drawing Sheets

Botanical designation: *Calibrachoa* sp.
Cultivar denomination: 'DUEALCOHOPI'.

BACKGROUND OF THE INVENTION

The present invention relates to a new and distinct cultivar of *Calibrachoa* plant, botanically known as *Calibrachoa* sp. and hereinafter referred to by the name 'Duealcohopi'.

The new *Calibrachoa* plant is a product of a planned breeding program conducted by the Inventor in Rheinberg, Germany. The objective of the breeding program is to create new compact *Calibrachoa* plants with unique bi-colored flowers.

The new *Calibrachoa* plant originated from a cross-pollination made by the Inventor in July, 2013 in Rheinberg, Germany of a proprietary selection of *Calibrachoa* sp. identified as code number AA12-006136-001, not patented, as the female, or seed, parent with a proprietary selection of *Calibrachoa* sp. identified as code number AA-000764-001, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2015.

Asexual reproduction of the new *Calibrachoa* plant by vegetative terminal cuttings in a controlled greenhouse environment in Rheinberg, Germany since July, 2015 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duealcohopi'. These characteristics in combination distinguish 'Duealcohopi' as a new and distinct *Calibrachoa* plant:

1. Compact, semi-upright to outwardly spreading, trailing and decumbent plant habit.
2. Freely branching habit.
3. Early and freely flowering habit.
4. Red purple-colored petals with a dark purple-colored central band and yellow-colored stripes.
5. Good garden performance.

The new *Calibrachoa* can be compared to plants of the female parent selection. Plants of the new *Calibrachoa* differ primarily from plants of the female parent selection in plant habit as plants of the new *Calibrachoa* are more compact than plants of the female parent selection. In addition, plants of the new *Calibrachoa* and the female parent selection differ in flower color as plants of the female parent selection have more pronounced yellow-colored stripes.

The new *Calibrachoa* can be compared to plants of the male parent selection. Plants of the new *Calibrachoa* differ primarily from plants of the male parent selection in flower color as plants of the male parent selection have salmon-colored flowers.

Plants of the new *Calibrachoa* can also be compared to plants of *Calibrachoa* sp. 'USCAL91001', disclosed in U.S. Plant Pat. No. 23,232. In side-by-side comparisons, plants of the new *Calibrachoa* differ primarily from plants of 'USCAL91001' in the following characteristics:

1. Plants of the new *Calibrachoa* are more compact than plants of 'USCAL91001'.
2. Plants of the new *Calibrachoa* have smaller leaves than plants of 'USCAL91001'.

3. Flower color of plants of the new *Calibrachoa* fades during the summer whereas flower color of plants of 'USCAL91001' does not fade during the summer.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet is a side perspective view of a typical flowering plant of 'Duealcohopi' grown in a container.

The photograph on the second sheet is a close-up view of typical flowers of 'Duealcohopi'.

DETAILED BOTANICAL DESCRIPTION

The aforementioned photographs and following observations, measurements and values describe plants grown during the summer in 12-cm containers in a glass-covered greenhouse in Rheinberg, Germany and under cultural practices typical of commercial *Calibrachoa* production. During the production of the plants, day and night temperatures averaged 18° C. and light levels averaged 4,500 lux. Rooted young plants were pinched one time three weeks after planting and were 16 weeks old when the photograph and description were taken. In the following description, color references are made to The Royal Horticultural Society Colour Chart, 2001 Edition, except where general terms of ordinary dictionary significance are used.

Botanical classification: *Calibrachoa* sp. 'Duealcohopi'.

Parentage:

*Female, or seed, parent*.—Proprietary selection of *Calibrachoa* sp. identified as code number AA12-006136-001, not patented.

*Male, or pollen, parent*.—Proprietary selection of *Calibrachoa* sp. identified as code number AA-000764-001, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; medium density.

Plant description:

*Plant and growth habit*.—Compact, semi-upright and outwardly spreading to trailing and decumbent plant habit; freely branching habit with about eleven primary lateral branches developing per plant; pinching enhances branching; dense and full appearance; vigorous growth habit; moderate growth rate.

*Plant height*.—About 22 cm.

*Plant diameter*.—About 67 cm.

Lateral branch description:

*Length*.—About 33 cm.

*Diameter*.—About 1.5 mm to 3 mm.

*Internode length*.—About 9 mm to 22 mm.

*Strength*.—Strong.

*Aspect*.—Initially upright to outwardly spreading to trailing and decumbent.

*Texture*.—Pubescent.

*Color*.—Close to 143A and 199A.

Leaf description:

*Arrangement*.—Before flowering, alternate, and after flowering, opposite; simple.

*Length*.—About 2 cm.

*Width*.—About 6.5 mm.

*Shape*.—Oblanceolate.

*Apex*.—Rounded.

*Base*.—Cuneate.

*Margin*.—Entire.

*Texture and luster, upper and lower surfaces*.—Pubescent; matte.

*Venation pattern*.—Pinnate; arcuate.

*Color*.—Developing leaves, upper surface: Close to 138A. Developing leaves, lower surface: Close to 138B. Fully expanded leaves, upper surface: Close to 137A; venation, close to 149A. Fully expanded leaves, lower surface: Close to 137A; venation, close to 149B.

*Petioles*.—Length: About 2.1 mm. Diameter: About 1.1 mm. Texture, upper and lower surfaces: Pubescent. Color, upper surface: Close to 145A. Color, lower surface: Close to 145B.

Flower description:

*Flower arrangement and habit*.—Single salverform flowers arising from leaf axils; freely flowering habit with usually about 150 to 170 flowers developing per plant; flowers face upright to outwardly.

*Fragrance*.—None detected.

*Natural flowering season*.—Early flowering habit, plants of the new *Calibrachoa* initiate and develop flowers about four to five weeks after planting; plants flower continuously from the spring throughout the summer in Germany.

*Flower longevity*.—Individual flowers last about seven to ten days on the plant; flowers not persistent.

*Flower diameter*.—About 2.8 cm.

*Flower length (height)*.—About 3.2 cm.

*Flower throat diameter*.—About 7.4 mm.

*Flower tube length*.—About 1.8 cm.

*Flower tube diameter, base*.—About 2.4 mm.

*Flower buds*.—Length: About 2.2 cm. Diameter: About 4.6 mm. Shape: Elongated oblong. Texture: Pubescent. Color: Close to 150B and 71A.

*Corolla*.—Arrangement: Five petals fused at the base and opening into a flared trumpet. Petal length from throat: About 1.4 cm. Petal lobe width: About 1.6 cm. Petal shape: Roughly spatulate. Petal apex: Rounded. Petal margin: Entire. Petal texture and luster, upper and lower surfaces: Smooth, glabrous; matte. Throat texture: Smooth, glabrous. Tube texture: Smooth, glabrous. Color: Petal, when opening, upper surface: Close to 67A. Petal, when opening, lower surface: Close to 70B. Petal, fully opened, upper surface: Ground color, close to 71C; central band, close to 79A; stripes and spots, close to 9A and 155A; venation, close to 59A and 71A; with development, ground color becoming closer to 82A and stripes and spots, closer to 10B and 10C. Petal, fully opened, lower surface: Close to 74C; venation, close to 149A. Throat: Close to 12A; venation, close to 159B. Tube: Close to 150C; venation, close to 149B.

*Calyx*.—Arrangement: Star-shaped calyx with five sepals; sepals fused at the base. Sepal length: About 1 cm. Sepal width: About 2 mm. Sepal shape: Lanceolate. Sepal apex: Acute. Sepal margin: Entire. Sepal texture and luster, upper and lower surfaces: Pubescent; matte. Color, upper surface: Close to 137A. Color, lower surface: Close to 137B.

*Peduncles*.—Length: About 1.2 cm. Diameter: About 1 mm. Angle: About 45° from stem axis. Strength: Moderately strong. Texture: Pubescent. Color: Close to 149B.

*Reproductive organs*.—Stamens: Quantity: Six per flower. Filament length: About 9 mm. Filament color: Close to 150C. Anther shape: Ellipsoidal. Anther length: About 0.8 mm. Anther color: Close to 153D. Pollen amount: Scarce. Pollen color: Close to 6A. Pistils: Quantity: One per flower. Pistil length: About 9.6 mm. Style length: About 8.4 mm. Style color: Close to 150A. Stigma shape: Ellipsoidal. Stigma color: Close to 149A. Ovary color: Close to 150A. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 5° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'Dueal-cohopi' as illustrated and described.

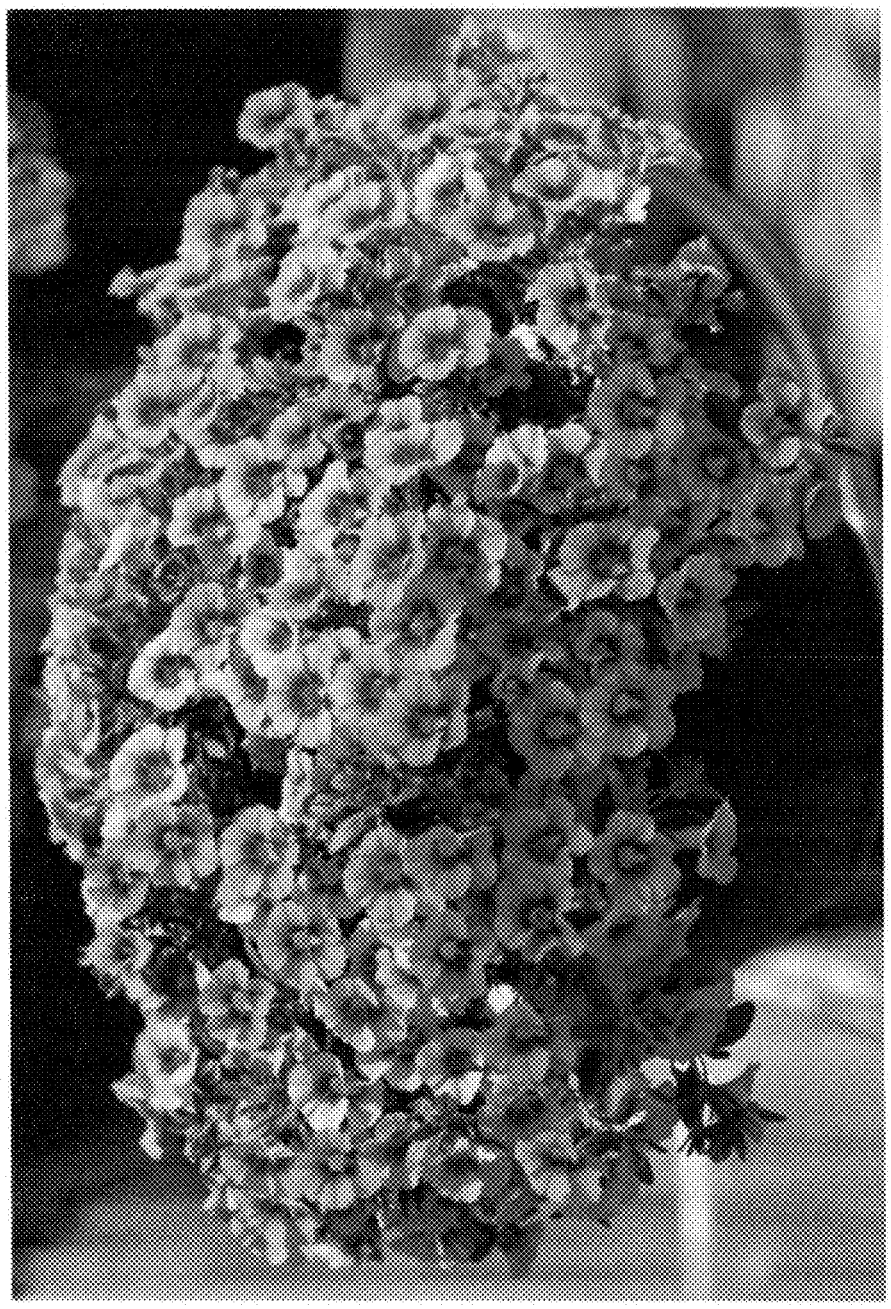

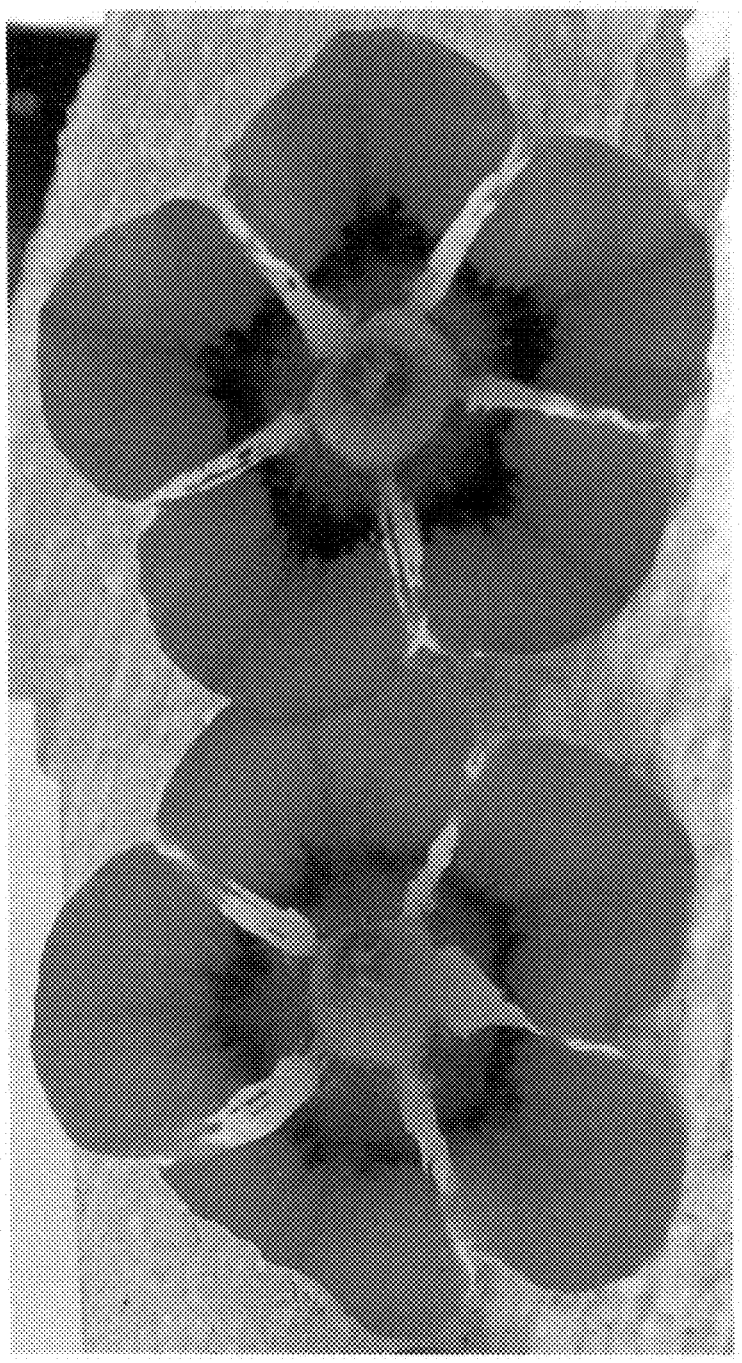

* * * * *